United States Patent [19]

Jenkins

[11] Patent Number: 5,200,614
[45] Date of Patent: Apr. 6, 1993

[54] ION MOBILITY SPECTROMETERS

[75] Inventor: Anthony Jenkins, North Reading, Mass.

[73] Assignee: Ion Track Instruments, Inc., Mass.

[21] Appl. No.: 821,681

[22] Filed: Jan. 16, 1992

[51] Int. Cl.$^5$ .......................... B01D 59/44; H01J 49/00
[52] U.S. Cl. ..................................... 250/286; 250/282; 250/287
[58] Field of Search ............... 250/281, 282, 286, 287, 250/288

[56] References Cited

U.S. PATENT DOCUMENTS

| | | | |
|---|---|---|---|
| 3,621,240 | 11/1971 | Cohen et al. | 250/287 |
| 3,742,213 | 6/1973 | Cohen et al. | 250/288 |
| 3,845,301 | 10/1974 | Wernlund et al. | |
| 4,238,678 | 12/1980 | Castleman et al. | 250/287 |
| 4,311,669 | 1/1982 | Spangler . | |
| 4,378,499 | 3/1983 | Spangler et al. | |
| 4,633,083 | 12/1986 | Knorr | 250/287 |
| 4,712,008 | 12/1987 | Vora et al. | 250/287 |
| 4,777,363 | 10/1988 | Eiceman et al. | 250/287 |
| 4,904,872 | 2/1990 | Grix et al. | 250/287 |

FOREIGN PATENT DOCUMENTS 0026683 4/1981 European Pat. Off. .
0253155 3/1988 European Pat. Off. .
2217103 10/1989 United Kingdom .

Primary Examiner—Bruce C. Anderson
Attorney, Agent, or Firm—Anthony J. Casella; Gerald E. Hespos

[57] ABSTRACT

An ion mobility spectrometer is provided which employs an electron capture process. A sample gas stream is irradiated to produce positive ions and electrons in an ionization chamber. An open grid electrode is employed in the ionization chamber to maintain a field-free space that allows ion population to build up in the ionization chamber. However, a high electric field is periodically generated across the ionization chamber for periods of less than one millisecond to cause most ions of one polarity in the ionization chamber to be swept out and into a drift chamber. Ions of opposite polarity are discharged on the walls of the ionization chamber. The ions entering the drift chamber travel at drift velocities dependant on their respective charge and mass. A collector electrode is provided for sequentially collecting ions of differing mass, and the collected ion current is transmitted to a signal processing means for measuring intensity and arrival times for the collected ions. A potential can be maintained between the drift chamber and the ionization chamber for preventing ions from traveling down the drift chamber. However, this potential between the drift chamber and the ionization chamber may periodically be switched synchronously with the generation of the field across the ionization chamber to enable ions to pass into the drift chamber during the switching.

14 Claims, 3 Drawing Sheets

ION MOBILITY SPECTROMETERS

BACKGROUND OF THE INVENTION

Ion mobility spectrometers are used to detect at least selected constituents in a stream of sample gas. An ion mobility spectrometer may be used, for example, to detect the presence of contaminants in air or to detect explosives.

Ion mobility spectrometers have been commercially available since about 1970. An early ion mobility spectrometer is disclosed, for example, in U.S. Pat. No. 3,699,333 which issued to Cohen et al. in 1972. Early work in ion mobility spectrometers also is described by Cohen and Karasek in the Journal of Chromatographic Science, Volume 8 pages 330-337 which was published in 1970. A full review of the theory of ion mobility spectrometry is provided in *Mobility and Diffusion of Ions in Gasses* by McDaniel and Mason which was published by John Wiley and Sons in 1973. Ion mobility spectrometers produced during the last 20 some years have all been fundamentally the same as the early on mobility spectrometer described by Cohen and Karasek.

A typical prior art ion mobility spectrometer is illustrated schematically in FIG. 1 and is identified generally by the numeral 10. The prior art ion mobility spectrometer 10 is comprised of two parts, namely, the ionization or reaction region 12 and the drift region 14 A sample of air to be analyzed is fed into the ionization region 12 on a stream of air or carrier gas containing a halogenated compound, such as methylene chloride. The carrier or air is ionized by the action of $\beta$ particles, which typically are emitted from a radioactive nickel[63] source, and which form positive ions and electrons. The electrons are all captured by oxygen or the halogen which is in vast excess in the ionization region 12 of prior art detector 10. The ions which are formed immediately come under the influence of an electric field $V_1$ in the ionization or reaction region 12, as shown in FIG. 1. The polarity of the field is set to direct the ions of interest (i.e. positive or negative) toward the drift region 14 of the prior art detector 10. For simplicity, only the negative ion analysis will be described here with respect to the prior art detector 10.

Sample molecules that are carried into the ionization or reactor region 12 of the prior art detector 10 may react with the negative ions present if the sample is more electro negative than the negative charge carrier. This type of ion molecule reaction is commonly known as charge transfer. Charge transfer processes can occur in areas of high field strength because there are many opportunities for dissipating the energy in the reacting bodies. However, the charge transfer efficiency in the prior art detector 10 employinq the prior art ion mobility spectrometer technology is very low.

Negative ions, including both sample and reactant ions are attracted toward a shutter grid 16 of the prior art detector 10 as shown in FIG. I. The shutter grid 16 has been essential to all prior art designs of ion mobility spectrometers and was first described by Bradbury and Nielson and was fully explained operationally by McDaniel and Mason in their above referenced work, *Mobility and Diffusion of Ions in Gasses*. Unfortunately, however, the shutter grid 16 of the prior art detector 10 only allows ions to pass through into the drift and collector region 14 for a short period of time, which typically is about 0.2 mS of duration and which occurs every 20 mS. At all other times, the ions arriving at the shutter grid 16 of the prior art detector 10 shown in FIG. 1 are discharged. This means that of the comparatively few molecules which were ionized, approximately 99% are annihilated in the prior art detector 10 before they can be detected. The total ionization and collection efficiency of the best prior art detector of the type shown in FIG. 1 is less than 0.01%. In view of this inherent inefficiency, prior art ion mobility spectrometers may fail to detect the presence of certain gases of interest which are in fact present in a sample of air being analyzed. For example, prior art ion mobility spectrometers that are used in bomb detectors may be unable to detect many of the organo nitro explosives, such as RDX. Additionally, the reactant ion in the prior art ion mobility spectrometer, usually $O_2^-$ or $Cl^-$, is likely to mask other light ions, thus making the prior art ion mobility spectrometer unsuitable for detection of such light ions.

In view of these deficiencies of the prior art detectors, it is an object of the subject invention to provide an improved and more efficient ion mobility spectrometer.

It is a further object of the subject invention to provide an ion mobility spectrometer that is much more effective in detecting the presence of explosive ions.

It is a further object of the subject invention to provide an ion mobility spectrometer that is particularly effective in detecting plastic explosives.

Still a further object of the subject invention is to provide a ion mobility spectrometer that is particularly effective for detecting light ions, such as oxygen and oxides of nitrogen and other atmospheric contaminants.

SUMMARY OF THE INVENTION

The subject invention is directed to a method and apparatus to vastly improve the efficiency, resolution and sensitivity of ion mobility spectrometers. The subject invention enables extremely low concentrations of electrophilic vapors, such as explosive vapors, to be detected where previously such detection was impossible. An additional advantage of the subject invention is gained by eliminating the reactant ion, and thereby enabling detection of other light ions such as the negative $NO_3$ ion which dissociates from certain explosive ions. The description of the invention presented herein will relate primarily to negative ion analysis. However, it will be appreciated that sensitivity to positive ions also will be improved by the apparatus and method of the subject invention.

The improved ion mobility spectrometer of the subject invention employs an electron capture process which provides a very high cross-section for capture at electron energy levels lower than a fraction of one electron volt. This provides an ionization efficiency that is much higher than the efficiency of the prior art charge transfer process and apparatus referred to above.

The electron capture process of the subject invention relates primarily to the ionization region and the start of the ion drift region of an ion mobility spectrometer. The latter part of the ion drift region and the collector of the subject ion mobility spectrometer may be of substantially conventional design.

The detector of the subject invention employs a stream of inert carrier gas, such as nitrogen, to feed the air sample to be tested for molecules of interest into the subject ion mobility spectrometer. The nitrogen carrier gas is irradiated with radiation from a radioactive source such as tritium or nickel[63] to form nitrogen positive ions and electrons. Electrophilic molecules react with the thermalised electrons by combination to form negative ions. Similarly, other non-electrophilic organic compounds may react with the $N_2$ ions to form organic positive ions.

The ionization chamber of the subject ion mobility spectrometer is a field-free region where the ion population, both electrons and positive ions, is allowed to build up by the action of the $\beta$ particles on the carrier gas. The high density of electrons produces a very high probability of ionization of the molecules of interest, and hence, an extremely high ionization efficiency.

As explained further herein, the apparatus and process of the subject invention achieves several very significant advantages. In particular, for negative ions, the process of ionization is improved significantly by changing from the prior art charge transfer process to an electron capture process. The reactant ion concentration (electrons or positive ions) is increased, thereby also increasing the probability of ionization. The subject apparatus does not employ a shutter grid as in the prior art and hence, there is no loss of ions by discharge onto a shutter grid. Ions that are accumulated over a 20 mS time period may be compressed into a pulse of 0.2 mS. This increases density and instantaneously collected current by a factor of 100. In the negative ion mode, there are no reactant ions in the subject apparatus to mask light ions which may be of interest, or other light ions produced by spontaneous dissociation from "heavy" ions. This is particularly important for the detection of many organo nitro explosive molecules, such as RDX, which dissociate after ionization. RDX is not normally detectable in prior art ion mobility spectrometers. Additionally, there is no distortion of the drift field by the large space charge produced by the reactant ion in the prior art ion mobility spectrometer. The electron space charge is removed in a few microseconds, and is well separated from all negative ions. This also reduces diffusion caused by the repulsive effect space charge, thus increasing resolution.

These and other advantageous combine to produce a more sensitive detector with better resolution than the prior art detector described above. These improvements allow the detector of the subject invention to detect vapors from extremely low volatility compounds, such as RDX, which is a common constituent of plastic explosives. For this particular application, the detector preferably is operated at an elevated temperature above 100° C.

DETAILED DESCRIPTION OF THE PREFERRED EMBODIMENT

Figure 1:
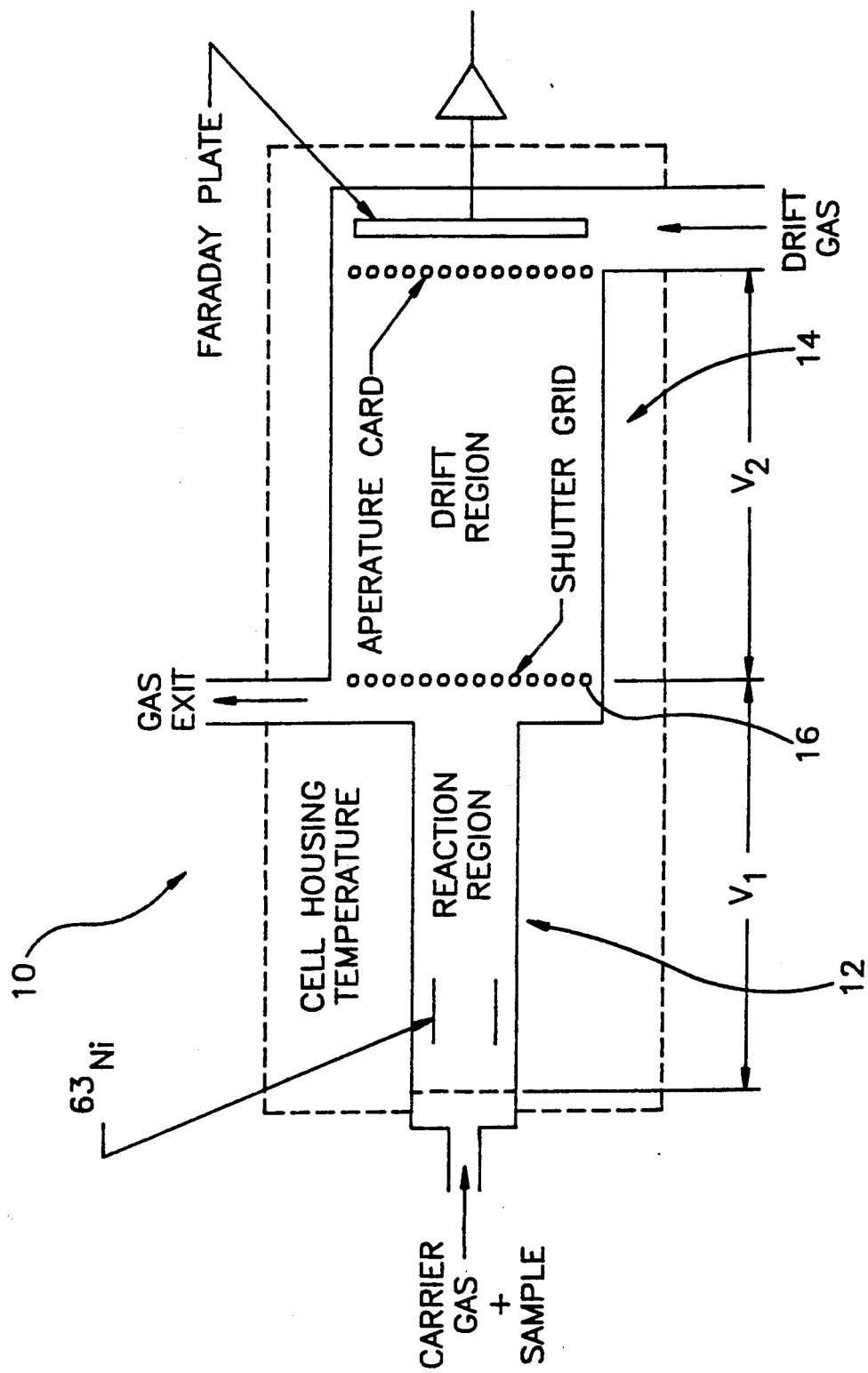
FIG. 1 is a schematic cross-sectional view of a prior art detector employing prior art ion mobility spectrometry.
Figure 2:
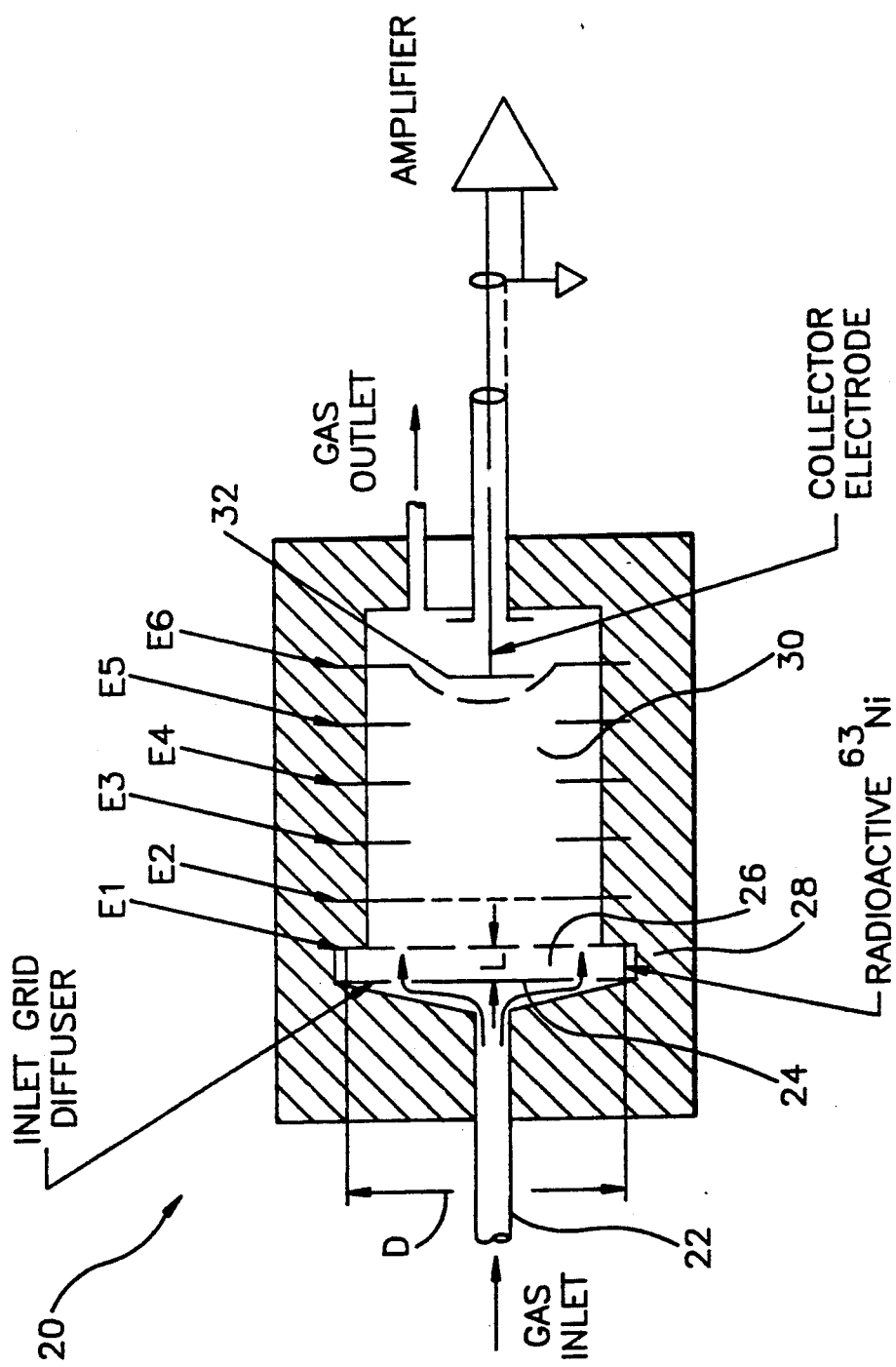
FIG. 2 is a cross-sectional view of a detector in accordance with the subject invention.

A detector in accordance with the subject invention is illustrated in FIG. 2 and is identified generally by the numeral 20. The detector 20 includes an inlet 22 into which sample molecules of interest are fed on a stream of nitrogen gas. It is to be understood, however, that other inert carrier gas may be used in place of nitrogen. For example, helium may be preferred for positive ion detection. The carrier gas and sample gas of interest are directed from the inlet 22 through a diffuser 24 and into an ionization chamber 26. The diffuser 24 is operative to spread the carrier gas and sample air of interest substantially uniformly across the ionization chamber 26. The inlet 22 and the diffuser 24 preferably are dimensioned and are operative to achieve a mean velocity of the carrier gas and sample air of interest through the ionization chamber 26 of about 1-5 mm/s.

The ionization chamber 26 is a shallow cylinder with a diameter "D" which preferably is in the range of 10-30 mm and a length "L" which preferably is in the range of 2-5 mm. The walls of the ionization chamber 26 comprise radioactive nickel[63] as shown in FIG. 2. As noted above, however, other radioactive sources, such as tritium, may be employed in place of the nickel[63]. The carrier gas and sample air of interest proceed through the ionization chamber 26 and exit through an open grid electrode $E_1$ into the ion drift region 30 having several field defining electrodes $E_2$-$E_n$.

Most of the time the grid electrode $E_1$ is maintained at the same potential as the remaining walls of the ionization chamber 22 to provide a largely field-free space. Electron and positive ion charges build up and sample molecules of interest react with the electrons to form negative ions.

The range of the $\beta$ particles from nickel[63] can be as long as 15 mm in the carrier gas in the detector 20. Thus, some of the primary $\beta$ particles may pass beyond the grid $E_1$ into the region between the grid $E_1$ and a second open grid electrode $E_2$ provided downstream in the ion drift region 30 of the detector 20. Further positive ions and electrons are generated in this region where they are not wanted. In order to prevent these ions from passing down the ion drift region 30 and being collected at the collector plate 32 at the end of the ion drift region 30, a potential of approximately 100 volts is maintained between the two grids $E_1$ and $E_2$ in the opposite direction to the field in the drift region between the open grid electrode $E_2$ and the collector plate 32. For negative ion analysis, the open grid electrode $E_2$ is held at between 100-200 volts more negative than the open grid electrode $E_1$. The resulting effect is that ions generated within the ionization chamber 26 stay contained in the ionization chamber 26, while ions generated in the region between the open grid electrodes $E_1$ and $E_2$ will drift towards one or the other of these grid electrodes $E_1$ and $E_2$ at speeds dependant on their mobility. Heavy ions are discharged within about 1-2 mS. However, electrons are discharged 1000 times faster or in between about 1-2 microseconds. This produces a net positive charge in this region, but no ions are allowed to escape into the remaining drift region 30 towards the collector electrode 32.

After a time of approximately 10-20 mS, the reaction or ionization region 26 contains positive ions, electrons and negative sample ions. The region between the open grid electrodes $E_1$ and $E_2$ contains electrons and positive ions. Periodically a field is established across the reaction or ionization region 26 by making the inlet diffuser 24 and radioactive source 28 more negative than the open grid electrode $E_1$. A high potential difference of between 500-1000 volts is switched on for between 0.1-0.2 mS. This is sufficient to sweep most of the negative ions from the reactor or ionization region 26 of the detector 20. At the same time that the field is switched across the reaction or ionization region 26, the field is also reversed between the open grid electrodes $E_1$ and $E_2$, so that the open grid electrode $E_1$ becomes more negative than the open grid electrode $E_2$. The potentials on each electrode for a negative ion analysis are shown graphically in FIGS. 3 and 3A.

Figures 3, 3A:
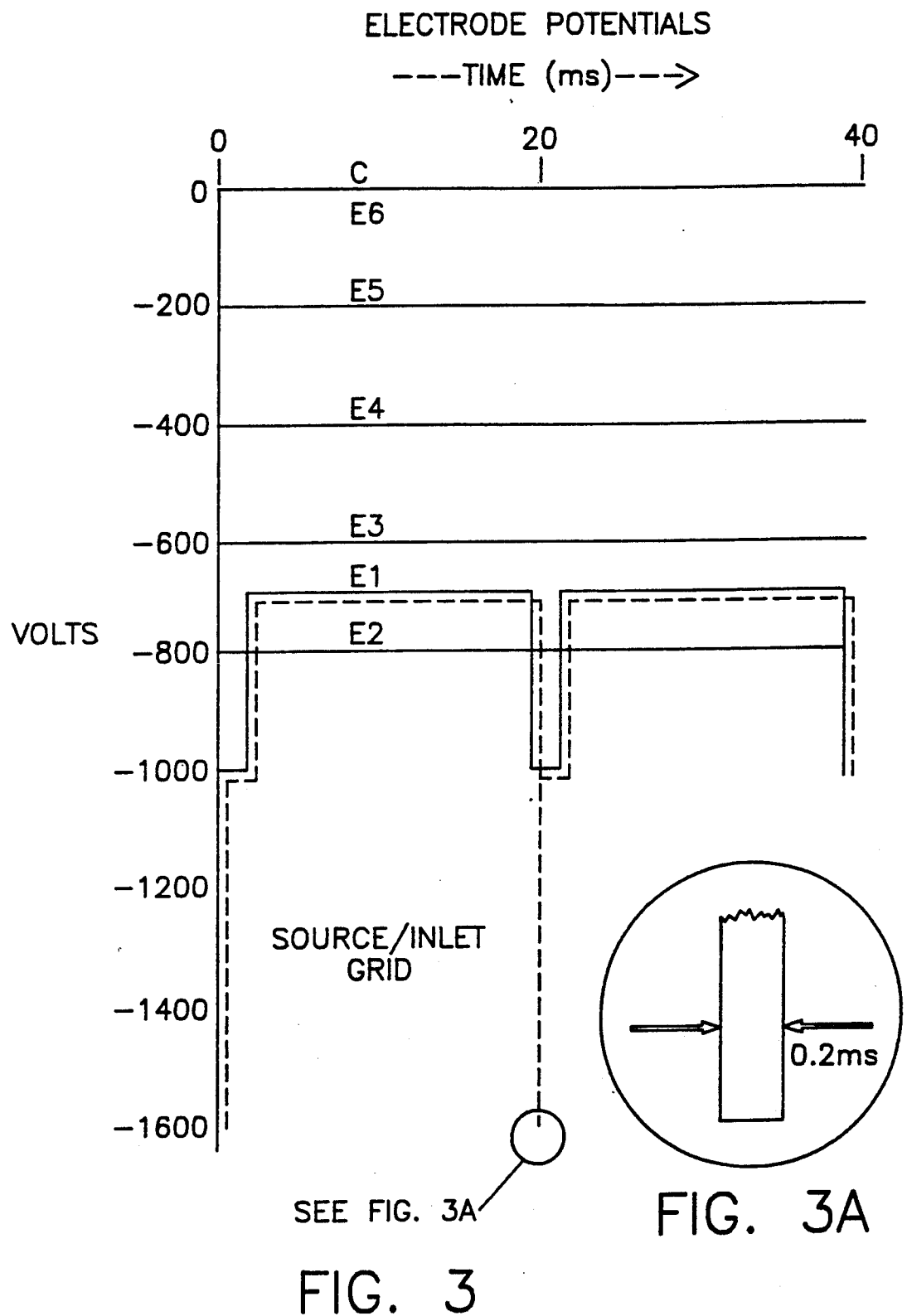
FIG. 3 is a graph showing electrode potentials.
FIG. 3A is an enlargement of a portion of the graph shown in FIG. 3.

After approximately 0.2 mS, the field across the reaction or ionization region 26 is again reduced to zero, and the ion population is again allowed to build up in the ionization chamber 26. Simultaneously, the negative ions which escaped from the reaction or ionization chamber 26 experience a constant electric field maintained by the annular electrodes $E_2$-$E_n$ down the drift region or tube 30 and move down the drift region 30 toward the collector electrode 32. The electrons also move down the drift region 30, but at a velocity approximately 1000 times as fast as the smallest negative ions. All electrons are cleared from the drift tube in less than approximately 100 microseconds. All of the negative ions pass through the open grid electrode $E_2$ within about 2 mS. After this time the field between the open grid electrodes $E_1$ and $E_2$ is again reversed as shown in FIG. 3. The negative ions continue to drift down the drift region 30 and arrive at the collector electrode 32 which is conveniently held at ground potential. The drift time varies from light ions to the heaviest ions from about 5 mS to about 18 mS. Electrons which are produced in the region between the open grid electrodes $E_1$ and $E_2$ during the period of approximately 2 mS that the open grid electrode $E_1$ is more negative then the open grid electrode $E_2$ also drift down the tube, but arrive no later then 2.1 mS of first switching the grids. Thus, the electrons are well separated from the lightest negative ions which arrive at the collector plate 32 in about 4 mS. Additionally, the electron capture process does not occur in this high field region, so that blurring of the ion peaks does not occur.

During the 2 mS period of the pulse, positive ions which existed in the region between the open grid electrodes $E_1$ and $E_2$ prior to the pulse and those which are produced during the pulse drift into the reaction or ionization chamber 26, but do not reach the inlet grid diffuser 24 before the field is removed. Thus, at the start of the period there is an excess of positive ions in the reaction or ionization chamber 26. This positive ion space charge acts to attract electrons and negative ions toward the center of the reaction region and away from the walls and grid where they would otherwise be discharged. This is an important advantage in containing the electron concentration and in not loosing negative ions after they have been formed.

For positive ion analysis, the fields and potentials are reversed from the embodiment described above, but timing sequences can remain the same.

While the invention has been described with respect to a preferred embodiment, it is apparent that various changes can be made without departing from the scope of the invention as defined by the appended claims.

I claim:

1. An apparatus for detecting constituents in a gas comprising:
   a ionization chamber;
   a gas inlet for delivering into the ionization chamber a sample gas stream to be tested for constituents;
   means for spreading the sample gas stream substantially evenly across the ionization chamber;
   a radioactive source for producing positive ions and electrons in the ionization chamber by irradiating a major portion of the sample gas stream and for producing other ions by combination or ion exchange with primary electrons and positive ions in the sample gas stream;
   a switchable open grid electrode in communication with the ionization chamber for defining an electric field within the ionization chamber;
   an elongate drift chamber in communication with the open grid electrode;
   switching means for periodically providing an electric field-free space within the ionization chamber to allow ion population to build up within the ionization chamber and for subsequently providing a high electric field across the ionization chamber, for a period of less than one millisecond, which periodically causes most ions of one polarity in the ionization chamber to be swept out of the ionization chamber through the open grid electrode and into the drift chamber, and which causes ions of opposite polarity to be discharged on walls of the ionization chamber;
   a collector electrode at an end of the drift chamber opposite the open grid electrode;
   means for providing an electric field in said drift chamber between the said open grid electrode and said collector electrode at the opposite end of the drift chamber for causing ions to travel through the drift chamber at drift velocities dependent on their respective charge and mass;
   means for sequentially collecting ions of differing mass and means for transmitting collected ion current to a signal processing means for measuring intensity and arrival time of the collected ions;
   whereby, the intensity and arrival time are indicative of the amount and identity of constituents of the sample gas stream.

2. An apparatus as in claim 1, wherein the ionizing radiation is provided by a $Ni^{63}$ beta source.

3. An apparatus as in claim 1 in which the ionization chamber is a shallow cylinder having a diameter between 10–30 mm and a length between approximately 2–5 mm.

4. An apparatus as in claim 1 in which the sample gas velocity is maintained below 5 mm/s.

5. An apparatus as in claim 1 in which the periodic electric field applied across the ionization chamber directs negative ions and electrons through the switchable open grid electrode into the drift chamber having an electric field which directs the negative ions and electrons towards the collector electrode.

6. An apparatus as in claim 1 in which the periodic electric field applied across the ionization chamber directs positive ions through the said first switchable open grid electrode into the said second elongate chamber having an electric field which directs the positive ions towards the said collector electrode.

7. An apparatus as in claim 1 in which the elongate drift chamber comprises a plurality of field defining electrodes of hollow cross section, the electric potential being uniformly reduced on each said field defining electrode towards the collector electrode.

8. An apparatus as in claim 7 comprising means for maintaining a potential between the open grid electrode and the first of the field defining electrodes;
   means for periodically switching the potential between the said electrodes to provide an electric field in a reverse direction to the remainder of the field in the elongate drift chamber thereby preventing any ions from travelling down the elongate drift chamber;

means for periodically switching the potential between the open grid electrode and the first of the field defining electrodes in the same direction as the remaining field down the elongate drift chamber, this field to be switched on for approximately between one and two milliseconds duration beginning synchronously with the application of the field across the ionization chamber to enable ions to pass into the said elongate drift chamber during the switching period.

9. An apparatus as in claim 8 in which the first field defining electrode comprises an open metallic mesh.

10. An apparatus as in claim 8 in which the potential between the open grid electrode and the first field defining electrode is switched from 100 to 200 volts to a value between 100 to 200 volts in the opposite polarity.

11. A method for detecting constituents in a gas comprising:

delivering a sample gas stream to be tested for the constituents into an ionization chamber;

spreading the sample gas stream substantially evenly across the ionization chamber;

irradiating a major portion of the sample gas stream for producing positive ions and electrons and for producing other molecular ions by combination or ion exchange with the produced positive ions and electrons in the sample gas stream;

providing an electric field-free space within the ionization chamber for allowing ion population to build up in the ionization chamber;

periodically providing a high electric field across the ionization chamber for a period of less than one millisecond for causing most ions of one polarity in the ionization chamber to be swept out of the ionization chamber and for causing ions of opposite polarity to be discharged on walls of the ionization chamber;

providing a drift chamber in communication with the ionization chamber and having a collector electrode at an end of the drift chamber remote from the ionization chamber;

providing an electric field in the drift chamber to cause ions to travel at drift velocities dependent on their respective charge and mass;

sequentially collecting ions of different mass; and transmitting collected ion current to a signal processing means for measuring intensity and arrival time of the collected ions, whereby the intensity and arrival time indicate the amount and identity of constituents of the sample gas stream.

12. A method as in claim 11, wherein the step of delivering a sample gas comprises maintaining gas velocity below 5 mm/s through the ionization chamber.

13. A method as in claim 11, wherein the step of providing an electric field-free space within the ionization chamber and periodically providing a high electric field across the ionization chamber is carried out by an open grid electrode in communication with the ionization chamber and wherein the step of providing an electric field in the drift chamber is carried out by a first field defining electrode in proximity to the ionization chamber and at least one additional field defining electrode spaced intermediate the first field defining electrode and the collector electrode, and wherein the method further comprises the steps of: maintaining a potential between the open grid electrode of the ionization chamber and the first of the field defining electrodes;

periodically switching the potential between said electrodes to provide an electric field in a reverse direction to the remainder of the field in the drift chamber for preventing ions from traveling down the elongate drift chamber from the ionization chamber; and periodically switching the potential between the open grid electrode and the first of the field defining electrodes to the same direction as the remaining field down the elongate drift chamber, this field being switched for approximately between one and two milliseconds beginning synchronously with the periodic application of the field across the ionization chamber for enabling ions to pass into said elongated drift chamber during the switching.

14. A method as in claim 13, wherein the potential between the open grid electrode of the ionization chamber and the first field defining electrode is switched from 100-200 volts to a value between 100-200 volts in the opposite polarity.

* * * * *